US00PP11217P

United States Patent [19]

Greeves

[11] Patent Number: Plant 11,217

[45] Date of Patent: Feb. 15, 2000

[54] *X CUPRESSOCYPARIS LEYLANDII* PLANT NAMED 'GRELIVE'

[75] Inventor: George Malcomson Greeves, Shropshire, United Kingdom

[73] Assignee: Plant Development Services Inc., Loxley, Ala.

[21] Appl. No.: 09/072,344

[22] Filed: Apr. 16, 1998

[51] Int. Cl.[7] ..... A01H 7/00

[52] U.S. Cl. ..... Plt./213

[58] Field of Search ..... Plt./213

[56] References Cited

PUBLICATIONS

UPOV–ROM GTITM computer database 1198/04 GTI JOUVE Retrieval Software, 2 citations for Grelive, 1993/96.

*Primary Examiner*—Howard J. Locker

*Assistant Examiner*—Wendy A Baker

[57] ABSTRACT

A new and distinct variety of *X Cupressocyparis leylandii* plant found as a sport of *X Cupressocyparis leylandii* 'Castlewellan Gold'. The new variety has an attractive soft green color and is superior in development of a dense, upright tree with a root system in better proportion to the top growth as compared to the species *X Cupressocyparis leylandii*.

1 Drawing Sheet

BACKGROUND OF THE INVENTION

This new variety of *X Cupressocyparis leylandii* was found as a sport of *X Cupressocyparis leylandii* 'Castlewellan Gold', an unpatented variety, maintained in the Breagh Nursery of Portadown, Northern Ireland. The sport, hereinafter referred to as 'Grelive', was discovered by George Malcomson Greeves in 1984. The new and distinct cultivar has attractive light green foliage, fast growth rate, and is naturally very full and dense.

Asexual propagation of the new plant by cuttings has been under Mr. Greeves' direction at the same location. Several generations of the new plant have been evaluated and the distinctive characteristics of the plant have remained stable. The plant cannot be reproduced true from seed.

In January of 1995, George M. Greeves sent the first 'Grelive' plants to PDSI (Plant Development Services Inc.) in Loxley, Ala. for evaluation. Here the plants have also shown stability of the distinctive characteristics.

SUMMARY OF THE INVENTION

The following are the most outstanding and distinguishing characteristics of this new cultivar when grown under normal horticultural practices in Portadown, Northern Ireland and Loxely, Ala.

1. Fast growth rate under normal fertilization and moisture conditions.
2. Naturally very bushy with a neat upright pyramidal shape.
3. The root system is in better proportion to the top growth as compared to the species.
4. Tolerates most soils from moist to dry and from sand to clay.
5. Salt tolerant.
6. Hardy to Zone 6.
7. Heat and drought tolerant.
8. Desirable in planters.

9. Good specimen plant.
10. Makes a good hedge or screen.
11. Easily propagated with semi-hardwood cuttings in summer, fall, or winter.
12. Attractive soft green color.
13. Tolerates sun to part shade.
14. Makes an attractive Christmas tree.
15. Plant can be pruned to maintain a certain shape or size.

DESCRIPTION OF THE DRAWINGS

This new variety of *X Cupressocyparis leylandii* is illustrated by the accompanying photographic prints in which.

Figure 1:
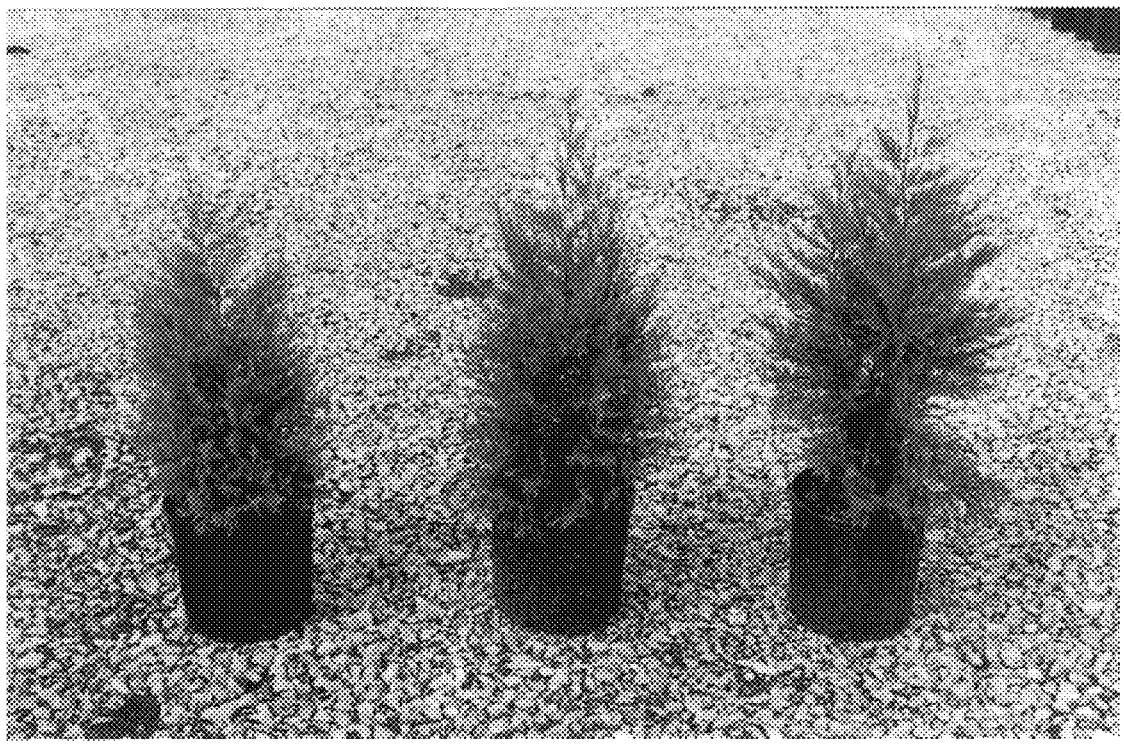
FIG. 1 is a side-by-side photograph of (from left to right) the parent of the new variety *X Cupressocyparis leylandii* 'Castlewelland Gold', the new variety, and an un-named specimen of the species *X Cupressocyparis leylandii*. The photograph shows the new variety's soft green color and its very dense broadly pyramidal shape.
Figure 2:
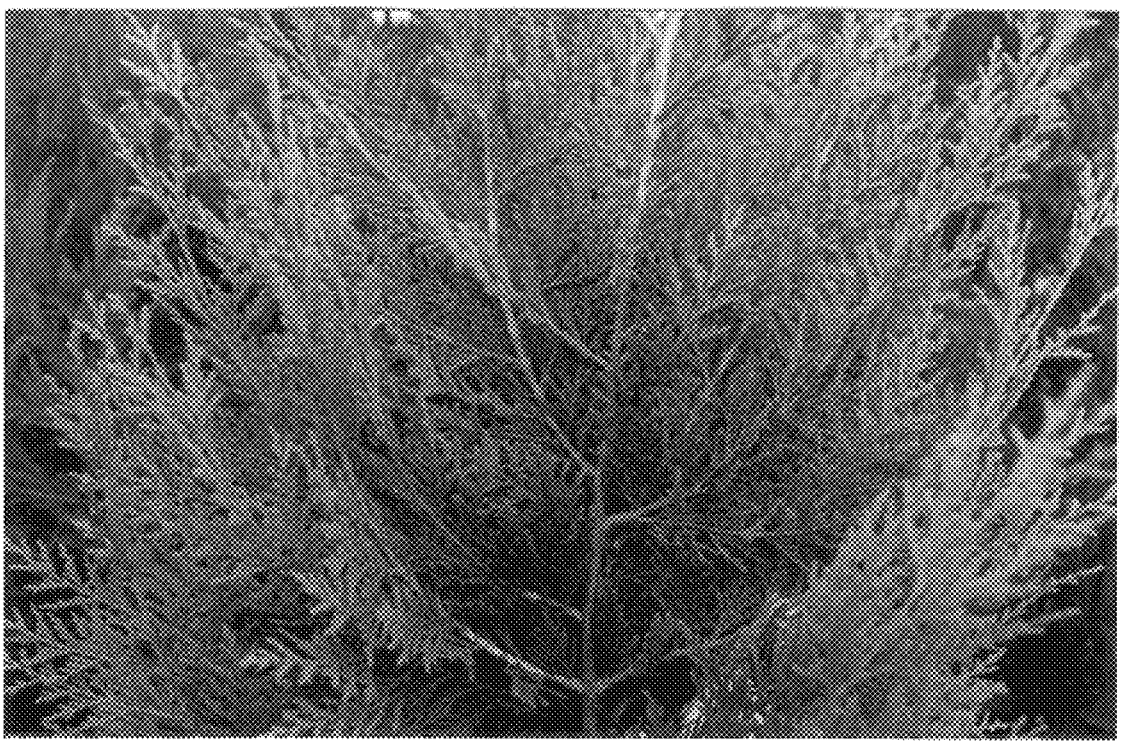
FIG. 2 shows a close-up of the foliage and stem characteristics of the new variety.

The colors shown are as true as is reasonably possible to obtain by conventional photographic procedures. The colors of the various plant parts are defined with reference to The Royal Horticultural Society Colour Chart. Descriptions of colors in ordinary terms are presented where appropriate for clarity in meaning.

BOTANICAL DESCRIPTION OF THE PLANT

The following is a detailed description of 'Grelive' based on my observations made of plants grown in wholesale commercial production practices and in greenhouses in Loxely, Ala.

| Characteristic | 'Grelive' | 'Castlewellan Gold' | 'Levland' |
|---|---|---|---|
| Height (Mature) | 40–50'+ | 40–50'+ | 60–70'+ |
| Width (Mature) | 20–30' | 20–30' | 20–30' |
| Follage Color (Immature) | Green G. 143B | Yellow-Green G. 144C | Yellow-Green G. 144A |
| Follage Color (Mature) | Green G. 137C | Green G. 138A | Green G. 137C |
| Habit | Very dense-broadly pyramidal | Dense-broadly pyramidal | Loose-pyramidal |

The new variety 'Grelive' was found in 1984 as a natural variation (sport) of *X Cupressocyparis leylandii* 'Castlewellan Gold' 'Castlewellan Gold' was found in Forest Park, Castlewellan, County Down, Ireland as an intergeneric hybrid between *Cupressus macrocarpa* 'Lutea' and *Chamaecyparis nootkatensis* and was put into commerce around 1970. The original author of the intergeneric hybrid name Cupressocyparis is William Dallimore (1871–1959) and the authors of the name Leylandii are Albert Bruce Jackson (1876–1947) and William Dallimore (1871–1959).

*X Cupressocyparis leylandii* (Leyland Cypress) is an intergeneric hybrid between *Cupressus macrocarpa* and *Chamaecyparis nootkatensis* and is very popular in the industry. It originated in 1888 in the garden of C. J. Leyland, Leighton Hall, Welshpool, England. This non-patented plant is comparable to the new plant yet there are important differences. 'Grelive' is naturally very bushy and the dense growth is evenly spread over the plant. It attains height quickly as a bushy plant with a single thin leader. Its root system is rapidly established and gives superior stability with less need of staking. Leyland Cypress also has a rapid growth rate, however, it produces a much less dense plant with a weaker root system. The foliage of the new variety has a soft green hue becoming darker towards the center of the plant. The light green tips enhance the overall appearance of the new plant. In addition, the scale-like foliage of the new variety is not as closely pressed to the stem as it is in the Leyland Cypress which results in a slightly more prickly plant.

Classification:

*Botanic.*—*X Cupressocyparis leylandii* 'Grelive'.

Form: Large, dense, and broadly pyramidal.

Height: 40–50' +.

Width: 20–30'.

Growth habit: Large, dense and broadly pyramidal. Fast growth rate under normal fertilization and moisture conditions.

Foliage: Scale-like leaves arranged in four ranked opposite pairs, closely pressed and overlapping, 1/8" to 3/8" long and 1/32" to 3/32 wide, apex acuminate, concave above and convex beneath. The upper and lower surface of the immature foliage is dull Green Group 143B and matures to Green Group 137C.

In 1996, the date of initial spring growth was March 15, in Loxley, Ala. After the initial spring flush there was almost continuous growth until that fall ending October 29, also in Loxley, Ala. When grown in full sun, the internode length is 1/16" to 1/4"; when grown in light shade the internode length is 1/8" to 3/8". As would be expected, a plant grown in shade results in a taller, less dense plant.

The average length of terminal growth of the initial spring flush is about 10" for a plant in full sun and about 12" when grown in shade. Liners 6 to 8" tall planted in three gallon containers during the winter finish in the fall at about 30" tall and 18" wide. There is no significant difference in vigor between this plant and the parent. Both the cultivar 'Grelive' and the species in general attain comparable height after a single growing season, however, 'Grelive' is considerably more dense due to the improved branching.

Stems: Branches are erect, flattened, and somewhat quadrangular. Young stems are Green Group 143B, turning a Greyed-Orange Group 175B in about sixty days. At this point, the scale-like leaves begin to fall off and the stems become scaly. As the stems mature into the winter they become Greyed-Green Group 197A and glabrous. The pith is solid and uniform. Young and older stems are densely branched.

Flowers: Monoecious, inconspicuous, borne on mature current season growth in the fall. Male flowers are Green Group 143B, 1/16" to 1/8" long by 1/16" to 1/8" wide, located terminally on lateral branchlets and fall off in six to eight weeks. Female flowers are Green Group 137C, 1/8" to 3/16" long by 1/16" to 1/8" wide, located axillary on lateral branchlets with 3/16" to 5/16" pedicels.

Fruit: Female cones are glaucous, Green Group 137D, globose, 5/8" to 3/4" across with eight woody peltate scales which usually contain five seeds per scale. Mature cones are Brown Group 200C. Seeds mature in one year and are Greyed-Orange Group 165A, rounded, disc-shaped samara, 3/16" long.

Culture: Grows well in a wide range of conditions, tolerates sun to part shade. Grows in nearly any soil type, from moist to dry and sand to clay. Responds well to mulching and medium applications of fertilizer; prefers ph of 5 to 7. Little pruning is needed. Can be sheared. Adaptable to containers and above ground planters. Propagated with semi-hardwood cuttings in summer, fall, or winter.

Pests: None serious.

I claim:

1. A new and unique variety of *X Cupressocyparis leylandii* plant named 'Grelive' as herein shown and described.

* * * * *